(12) United States Patent
Gevers et al.

(10) Patent No.: US 10,689,612 B2
(45) Date of Patent: Jun. 23, 2020

(54) METHOD TO PURIFY COCCIDIAL OOCYSTS FROM ANIMAL FAECES, A SYSTEM SUITABLE FOR APPLYING THIS METHOD AND OOCYSTS OBTAINED THEREWITH

(71) Applicant: Intervet inc., Madison, NJ (US)

(72) Inventors: Koen Gevers, Boxmeer (NL); Theodorus Petrus Maria Schetters, Cuijk (NL)

(73) Assignee: Intervet Inc., Madison, NJ (US)

(*) Notice: Subject to any disclaimer, the term of this patent is extended or adjusted under 35 U.S.C. 154(b) by 405 days.

(21) Appl. No.: 15/300,499

(22) PCT Filed: Apr. 2, 2015

(86) PCT No.: PCT/EP2015/057294
§ 371 (c)(1),
(2) Date: Sep. 29, 2016

(87) PCT Pub. No.: WO2015/150512
PCT Pub. Date: Oct. 8, 2015

(65) Prior Publication Data
US 2017/0121670 A1 May 4, 2017

(30) Foreign Application Priority Data
Apr. 3, 2014 (EP) .................................. 14163340

(51) Int. Cl.
*C12N 1/10* (2006.01)
*C12N 1/02* (2006.01)
(Continued)

(52) U.S. Cl.
CPC .................. *C12N 1/10* (2013.01); *B07B 1/18* (2013.01); *B07B 1/22* (2013.01); *C12N 1/02* (2013.01); *B07B 1/10* (2013.01)

(58) Field of Classification Search
CPC .... C12N 1/02; C12N 1/10; B07B 1/10; B07B 1/18; B07B 1/22; C12M 27/10;
(Continued)

(56) References Cited

U.S. PATENT DOCUMENTS 5,196,313 A    3/1993  Culbreth
5,888,748 A    3/1999  Crabb
(Continued)

FOREIGN PATENT DOCUMENTS

CN    101430281    * 5/2009    ............. G01N 21/64
CN    101430281 A  * 5/2009
(Continued)

OTHER PUBLICATIONS

Detecting Cryptosporidiumoocyst and Giardiacyst in drinking water, WPI/Thomson, May 13, 2009, Week 200966, Thomson Scientific, London GB, AN 2009-J46422, XP002733899.
(Continued)

*Primary Examiner* — Charles A Fox
*Assistant Examiner* — Kalyanavenkateshware Kumar

(57) ABSTRACT

The invention pertains to a method to purify coccidial oocysts having dimensions between Dmin and Dmax from faeces comprising the steps of collecting the faeces containing the coccidial oocysts from host animals, diluting the faeces in an aqueous medium, separating a coarse fraction comprising macroscopic particulate matter from the diluted faeces and collecting an aqueous fraction containing the oocysts, characterised in that the method further comprises sieving the aqueous fraction over a first sieve deck having mesh openings to let the oocysts pass, to obtain an aqueous filtrate comprising the oocysts and a first residue comprising particles larger than the oocysts, and sieving the aqueous filtrate over a second sieve deck having mesh openings to obstruct passing of the oocysts through this sieve deck, to
(Continued)

Figure 1:
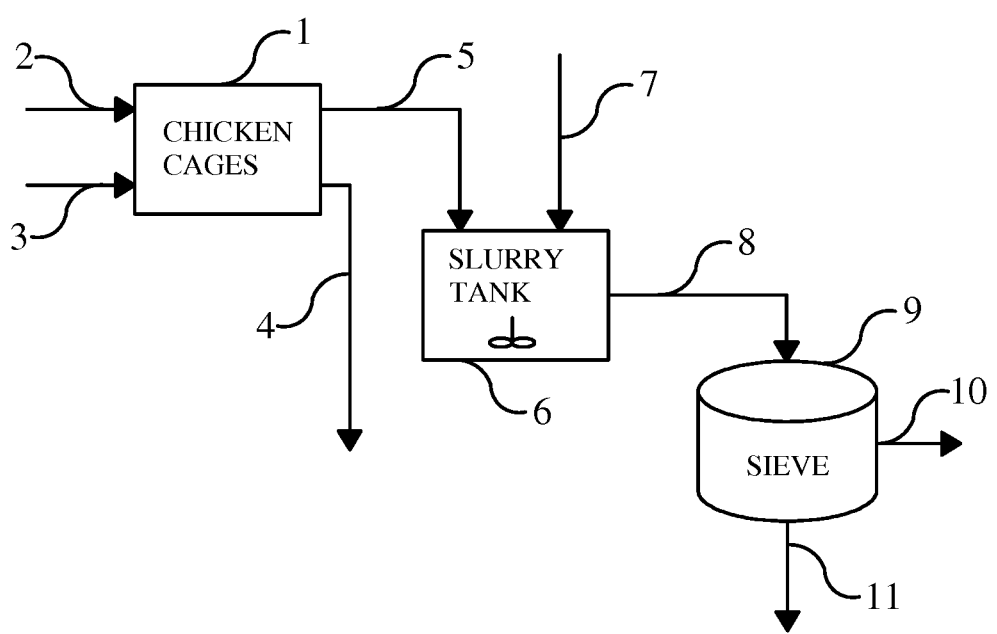
Figure 2:
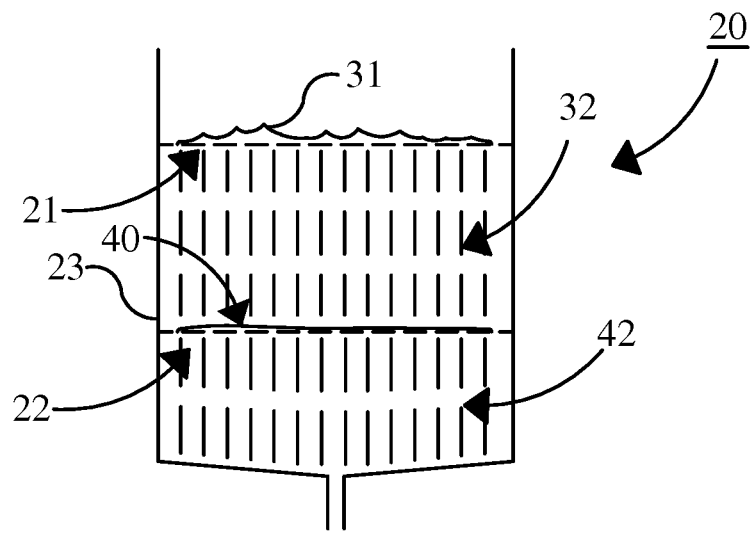

obtain a second residue comprising the purified oocysts and a waist filtrate comprising particles smaller than the oocysts. The invention also pertains to a system suitable for applying this method and to oocysts obtained therewith.

10 Claims, 4 Drawing Sheets

(51) Int. Cl.
  *B07B 1/18* (2006.01)
  *B07B 1/22* (2006.01)
  *B07B 1/10* (2006.01)

(58) Field of Classification Search
  CPC ...... C12M 29/04; C12M 29/06; C12M 33/14; C12M 45/02; C12M 47/02
  See application file for complete search history.

(56) References Cited

U.S. PATENT DOCUMENTS

| | | | |
|---|---|---|---|
| 2002/0160022 A1 | 10/2002 | Schasteen | |
| 2008/0194006 A1 | 8/2008 | Hutchins | |
| 2012/0122183 A1* | 5/2012 | Pedersen | C12N 1/02 435/198 |
| 2013/0040290 A1 | 2/2013 | Halden | |
| 2015/0360202 A1* | 12/2015 | Ito | A01K 1/015 252/194 |

FOREIGN PATENT DOCUMENTS

| | | |
|---|---|---|
| JP | 2008-178864 A | 8/2008 |
| RU | 2233713 C2 | 8/2004 |
| WO | 2003020917 A1 | 3/2003 |
| WO | 2013043122 A1 | 3/2013 |

OTHER PUBLICATIONS

European Search Report for EP application 14163340.4 dated Jan. 16, 2015, 3 pages.
International Search Report for PCT EP application 057294 dated Jun. 9, 2015, 4 pages.
McKenna PB, et al, Recovery of Sarcocystis gigantea sporocysts from cat faeces, Veterinary Parasitology, Jan. 1, 1988, pp. 215-227, vol. 26, No. 3-4.
Perrine, D et al, Efficacié de l'oznation des eaux sur l'inactivation des oocystes de Cryptosporidium, Bulletin de l'academie national de médecine, Jun. 1990, pp. 845, vol. 174, No. 6.
Riggs, MW et al, Infectivity and neutralization of Cryptosporidium parvum sporozoites, Infection and Immunity, Sep. 1, 1987, pp. 2081-2087, vol. 55, No. 9.
Waldenstedt, L et al, Sporulation of Eimeria maxima Oocysts in Litter with Different Moisture Contents, Poultry Science, Oct. 2001, pp. 1412-1415, vol. 80, No. 10.
Wee, SH et al, Isolation of Cryptosporidium parvum oocysts from fecal samples—the combination of ether extraction and discontinuous sucrose gradients, The Korean journal of parasitology, Mar. 1994, pp. 7-12, vol. 32, No. 1.
Laboratory Technical Manual for Veterinary Parasitology, The UK Ministry of Agriculture, Fishery and Food, rabit coccidiosis, Dec. 31, 1982, pp. 48, 51.

* cited by examiner

METHOD TO PURIFY COCCIDIAL OOCYSTS FROM ANIMAL FAECES, A SYSTEM SUITABLE FOR APPLYING THIS METHOD AND OOCYSTS OBTAINED THEREWITH

CROSS-REFERENCE TO RELATED APPLICATIONS

This application is a national stage entry under 35 U.S.C. § 371 of PCT/EP2015/057294 filed on Apr. 2, 2015, which claims priority to EP Application No. EP14163340.4 filed on Apr. 3, 2014. The content of PCT/EP2015/057294 is hereby incorporated by reference in its entirety.

GENERAL FIELD OF THE INVENTION

The present invention pertains to a method to purify coccidial oocysts having dimensions between Dmin and Dmax from faeces, comprising the steps of collecting the faeces containing the coccidial oocysts from host animals, diluting the faeces in an aqueous medium, optionally separating a coarse fraction comprising macroscopic particulate matter from the diluted faeces, and collecting an aqueous fraction (which could be the faeces diluted in the aqueous medium) containing the oocysts in order to retrieve the oocysts therefrom. The invention also pertains to a system suitable for applying this method and to oocysts obtained therewith.

BACKGROUND OF THE INVENTION

Coccidiosis is a disease of various animals in which the intestinal mucosa is invaded and damaged by a protozoa of the subclass Coccidia. The economic effects of coccidiosis can be especially severe in the poultry industry where intensive housing of birds favors the spread of the disease. Infection by coccidial protozoa is, for the most part, species specific. Numerous species, however, can infect a single host. For example, there are seven species of coccidial protozoa which infect chickens, six of which are considered to be moderately to severely pathogenic.

The life cycle of the coccidial parasite is complex. For example, protozoa of the genera *Eimeria, Isospora, Cystoisospora,* or *Cryptosporidium* typically only require a single host to complete their life cycle, although *Cystoisospora* may utilize an intermediate host. Under natural conditions, the life cycle begins with the ingestion of sporulated oocysts from the environment. Oocysts are generally ovoid to ellipsoid in shape, range from 10-48 µm in length by 10-30 µm in width, and may contain specialized structures, such as polar caps, micropyles, residual and crystalline bodies. When sporulated oocysts are ingested by a susceptible animal, the wall of the sporulated oocyst is broken in order to release the sporocysts inside. In poultry, the release of the sporocyst is the result of mechanical disruption of the sporulated oocyst in the gizzard. Within the sporocysts, are the sporozoites which are the infective stage of the organism. In poultry, the breakdown of the sporocyst coat and release of the sporozoites is accomplished biochemically through the action of chymotrypsin and bile salts in the small intestine. Once released, the sporozoites invade the intestinal mucosa or epithelial cells in other locations. The site of infection is characteristic of the species involved. For example, in the genus *Eimeria, E. tenella* is localized in the ceca; *E. necatrix* is found in the anterior and middle portions of the small intestine; *E. acervulina* and *E. praecox* occur in the upper half of the small intestine; *E. brunetti* occurs in the lower small intestine, rectum, ceca, and cloaca; *E. mitis* is found in the lower small intestine, while *E. maxima* can be found in any of these physiological locations.

Once inside the host animals' cells, sporozoites develop into multinucleate meronts, also called schizonts. Each nucleus of the meront develops into an infective body called a merozoite which enters new cells and repeats the process. After a variable number of asexual generations, merozoites develop into either microgametocytes or macrogametes. Microgametocytes develop into many microgametes which, in turn, fertilize the macrogametes. A resistant coat then forms around the resulting zygotes. The encysted zygotes are called oocysts and are shed unsporulated in the faeces. Infected birds may shed oocysts in the faeces for days or weeks. Under proper conditions of temperature and moisture, the oocysts become infective through the process of sporulation. Susceptible birds then ingest the sporulated oocysts through normal pecking activities or ground/litter foraging and the cycle repeats itself. Ingestion of viable, sporulated oocysts is the only natural means of infection. Infection with coccidial protozoa results in immunity so that the incidence of the disease decreases over time as members of the flock become immune. This self-limiting nature of coccidial infections is widely known in chickens and other poultry. The immunity conferred, however, is species specific such that introduction of another species of coccidial protozoa will result in a new disease outbreak.

The oocyst wall of coccidial protozoa provides a highly effective barrier for oocyst survival. Oocysts may survive for many weeks outside the host. In the laboratory, intact oocysts are resistant to extremes in pH, detergents, proteolytic, glycolytic, and lipolytic enzymes, mechanical disruption, and chemicals such as sodium hypochlorite and dichromate.

Two methods are currently used to control coccidiosis in poultry. The first involves control by chemotherapy. Numerous drugs are available for the control of coccidiosis in poultry. Because of the number of species which cause the disease, very few drugs are efficacious against all species, although a single drug may be efficacious against several species. In modern broiler chicken production, for example, administration of drugs to control coccidiosis is routine. The expense for preventative medication against coccidiosis represents a significant cost of production.

Vaccination of birds against coccidiosis is an alternative to chemotherapy. An advantage of vaccination is that it can greatly reduce or eliminate the need to administer anticoccidial drugs, thus reducing drug costs to poultry producers, preventing the development of drug-resistant strains, and lessening consumer concerns about drug residues. Numerous methods have been developed to immunize poultry against coccidial protozoa. The successful methods have all been based on the administration of live protozoa, either fully virulent strains or attenuated strains. The most common route of administration is oral, although other routes have been used. Typically, chickens are vaccinated by oral administration either directly into the mouth or via the feed or water of viable sporulated oocysts.

Regardless of the route of administration, procedures for the production of coccidiosis vaccines are quite similar. Briefly, coccidial protozoa are produced by infecting host animals with a single species of coccidial protozoa. These "seed stocks" are often clonal in nature, that is, derived from a single organism in order to insure the presence of only the species of interest. Seed stocks may be wild type, that is, isolated from the field, or they may be precocious or attenuated strains. The protozoa are then allowed to undergo replication in the host, after which, protozoa are collected from the animals, usually from the excreta. The use of attenuated strains typically results in fewer shed oocysts from the host animal. In a first step of the purification process, if needed, a coarse fraction comprising macroscopic particulate matter is separated from diluted excreta. The protozoa are then separated from the diluted excreta by well known techniques such as salt floatation and centrifugation (to ensure that no particulate matter having a density that is more than 10% different from the density of the oocysts is purified with the oocysts). At the time of collection, the protozoa are at the non-infective oocyst stage of the life cycle. In order to become infective, and therefore useful for vaccines, the oocysts must be induced to undergo sporulation. In members of the genus *Eimeria*, sporulation typically involves the incubating the oocysts in a 1% to 4% aqueous solution of potassium dichromate at 19° C. to 37° C., preferably around 28° C. with constant aeration. Sporulation is usually complete within 12 to 48 hours depending on the temperature used. Monitoring of the sporulation process is accomplished by microscopic examination of the protozoa. Storage compositions found in the prior art typically include an aqueous solution of potassium dichromate. The sporulated oocysts are usually stored in 1 to 4% aqueous solution of potassium dichromate to prevent bacterial growth, however, other storage media have been used.

Current vaccines available for the prevention of coccidiosis typically contain a 2.5% weight to volume solution and contain approximately 1,600 oocysts per dose (400 sporulated oocysts representing four different species). An important disadvantage of the current methods to obtain sporulated oocysts is that they typically depend on salt flotation and centrifugation for purification. This is not only very time consuming (in particular centrifugation has to take place batchwise) but also leads to the oocysts being in contact with a concentrated salt solution for many hours. The amount of water in relation to the amount of oocysts has to be kept low since otherwise the batch wise centrifugation step would be far from economical. The net effect of all this, in particular the long process time and the contact of the oocysts with concentrated salt, is that up to 80% of the viable oocysts gets lost during this known purification process. Also, the purified oocysts contain residues of the salts used for the flotation technique, which salt is disadvantages in further process steps or which alt might even be incorporated in the ultimate vaccine and interfere with the vaccine constituents or the host animal. Also, the oocysts get contaminated with the solutes typically used in the centrifugation technique for building up a density gradient. This is another disadvantage of the prior art methods.

OBJECT OF THE INVENTION

It is an object of the present invention to devise a method that mitigates disadvantages of prior art oocysts purification methods, in particular to devise a method wherein a large part of the oocysts is purified while still being viable and able to sporulate. It is also an object of the invention to devise a system for applying this method and to oocysts purified therewith, preferably not having the disadvantage of salt or other solute residues being present.

SUMMARY OF THE INVENTION

In order to meet the first object of the invention a method according the GENERAL FIELD OF THE INVENTION section has been devised wherein in order to retrieve the oocysts from the aqueous fraction, the method comprises the steps of sieving the aqueous fraction over a first sieve deck having mesh openings to let the oocysts pass, to obtain an aqueous filtrate comprising the oocysts and a first residue comprising particles larger than the oocysts, and thereafter sieving the aqueous filtrate over a second sieve deck having mesh openings to obstruct passing of the oocysts through this sieve deck, to obtain a second residue comprising the purified oocysts and a waist filtrate comprising particles smaller than the oocysts.

Applicant found that by applying a simple two-step sieving process, oocysts can be purified to an adequate level from the aqueous fraction of the faeces. In the first sieving step the particles coarser than the oocysts (typically sand grains, grit and remains of plants) can be removed, while in the second sieving step the particles smaller than the oocysts (typically bacteria, viruses, digested remains of plants, protein flocks, oil droplets etc.) can be removed. This way an oocysts fraction may be obtained that has very low load of (or even virtually none) contaminating microbes, whereas with using prior art flotation methods, the oocysts fraction still contains a considerable load of microbes. Sieving can be applied (semi-) continuously and the amount of water present in the aqueous fraction in relation to the amount of oocysts is not bound to any economical maximum: the water ultimately passes the second sieve deck while the purified oocysts remain as a thin layer residue on this deck. This way, water can be effectively used to obtain a good sieving and cleaning action.

In the art, sieving has never been used or even suggested as a method to purify coccidial oocysts from faeces. Although sieving has been used to remove a coarse fraction from the faeces, it has never been used to obtain purified oocysts. Without being bound to theory, there appear to be several reasons for this. Firstly, the common methods used for purifying oocysts are all based on using the particular density of the oocysts, since it is understood that in the faeces, no other major fractions are present that have the same density (i.e. having a density within a density range being at most 10%, or even at most 9, 8, 7, 6, 5, 4, 3, 2 or even as little as 1% different from the density of the oocysts) as the oocysts. Therefore, such methods can lead to an adequately pure oocysts containing composition. With sieving, one cannot discriminate between particles having different densities, but only between particles having different sizes (different sieving properties). This inherently leads to the fact that with sieving, other particles in the same size range as the oocysts, but having another density are incorporated as an additional contamination in the oocysts fraction. Therefore it is commonly expected that with sieving the oocysts cannot be purified to an adequate level. Also, oocysts are not perfectly spherical but generally ovoid to ellipsoid in shape. Sieving non-spherical particles has the inherent problem that the sieving action depends on the orientation particles take with regard to the sieve deck. Since this orientation cannot be controlled, sieving is often not regarded a viable option for precisely fractioning non spherical particles. Lastly, sieving often leads to a high mechanical load on the particles being sieved, in particular when the mesh size is in the same range of the particle size. For biological matter, such a high mechanical load is often detrimental for their viability (cf. the commonly used French Press method for killing bacteria). To applicant's surprise, none of all this prevents sieving from being a good method to purify coccidial oocysts from faeces and obtain a purity that is adequate for using the oocysts in an effective vaccine.

As any person skilled in the art of sieving knows, it is noted that "having mesh openings to let the oocysts pass" not simply equates "having mesh openings larger than the largest dimension of the oocysts", nor that "having mesh openings to obstruct passing of the oocysts" simply equates "having "mesh openings smaller than the smallest dimension of the oocysts". As commonly known, whether or not a particle having particular dimensions passes the sieve deck (thus whether or not the mesh openings let the particle pass) not only depends on the particle dimensions in relation to the size of the openings, but also depends on wire material of the sieve deck, wire thickness, type of mesh (woven, the type of weave, sputtered, milled, laser ablated, drilled etc), the form of the mesh openings, whether or not the sieve deck is vibrated, the amplitude of vibration, whether or not additional fluid is used to help particles to pass the sieve deck, the shape of particles etc. For example, a sieve deck having mesh openings of 150 μm, under the circumstances that the deck is not vibrated, may be able to let only particles having a diameter of less than 50 μm pass (since typically "bridges" of 2-3 particles may form on a mesh opening). Other circumstances may also play a role. For example, a sieve having mesh openings of 100 μm may be able to let pass particles with an upper limit in size of 30 μm, or for example 60 μm or even for example 99 μm depending on the amount of lubricant (typically water) used and the amount of vibration of the deck. Correspondingly, this is true for the situation in which the mesh openings are such that they should obstruct the passage of the particle. Using common general knowledge from the art of sieving, the skilled person can devise a sieving set up that can be used according to the present invention.

Another advantage of the present invention is that the purified oocysts do no longer need to contain (substantially) all oocysts present in the faeces. With the present method one can choose a size range of oocysts one desires to purify. With the prior art methods, all oocysts of a certain density are purified as one fraction. With the current method it is for example possible to leave out the smallest oocysts, or chose for example only the fraction that represents certain coccidial species (each species has typical sizes ranges for its oocysts).

In order to meet the second object of the invention a system suitable for purifying coccidial oocysts having dimensions between Dmin and Dmax from faeces or a fine fraction thereof, has been devised, the system comprising a first endless shaped sieve deck having mesh openings suitable to let the oocysts pass the sieve deck in a filtrate and obstruct particles larger than the oocysts, means for automatically loading the filtrate to the inside of second endless shaped sieve deck, wherein the second sieve deck has mesh openings to obstruct passing of the oocysts through this sieve deck and let particles smaller than the oocysts pass.

In order to meet the third object of the invention, the invention provides a purified coccidial oocysts composition obtained using the above described method or system, wherein the composition contains particles having dimensions between Dmin and Dmax and having a density different from the density of the oocysts.

Definitions

A oocysts composition purified from faeces means that at least 90%, in particular 91, 92, 93, 94, 95% or more of the non-oocysts material is removed from the faeces wherein the oocysts were excreted.

Dmin of a particle is a minimum dimension (length, width or height) of that particle.

Dmax of a particle is a maximum dimension (length, width or height) of that particle.

A macroscopic object: an object that can be seen with the unaided human eye. Typically, this means that the object has a dimension of at least about 0.1 mm.

A particle is a localized microscopic or macroscopic object to which can be ascribed physical properties such as volume and mass. Typical particles present in animal faeces are sand grains, silt particles, clay particles, remains of plants (digested and undigested), oil droplets, bacteria, viruses, grit, pebbles etc.

A mesh opening of a sieve deck is equal to the diameter of an imaginary circle that fits the actual opening in the deck. A mesh opening is inherently "around" a predetermined size since a surface with multiple mesh openings cannot be made with exactly the same dimension for all openings, and also is subject to variation under mechanical load (mass on sieve deck, vibrating etc). A mesh opening is typically an effective average around a predetermined size. In this respect "around value X" for a mesh size means than in practice the actual size of an opening may vary between 0.9 and 1.1 times X, in particular between 0.95 and 1.05 times X, and preferably between 0.98 and 1.02 times X.

Automatically means without operator intervention. Automatically does not rule out that an operation is operator initiated or stopped.

EMBODIMENTS

In a first embodiment the first sieve deck has mesh openings larger than Dmin and up to Dmax and the second sieve deck has mesh openings around Dmin. With regard to the second sieve deck, it was found that if the mesh openings are around Dmin, that any oocysts having a smallest dimension of Dmin are obstructed in passing the deck, while bacteria, viruses, protein flocks and other particles having a typical dimension smaller than Dmin may pass the deck. This way an oocysts fraction may be obtained that is virtually sterile. A critical situation could be arrived at if the aqueous fraction to be filtered would have too many non-oocyst particles having a dimension just below Dmin, since such particles would typically also be somewhat obstructed by the deck and might thus remain as a contamination in the oocysts residue. However, such critical particles appear to be not (reasonably noticeable) present in animal faeces of various kinds, and thus, using a mesh size around Dmin appears to be perfectly suitable to keep the oocysts in the residue while smaller contaminant particles will pass this sieve deck. With regard to the first sieve deck, it is obvious that the mesh openings preferably at least the size of Dmin. However, the preferable maximum size is not obvious per se. A size above Dmin but substantially below Dmax could be adequate if for example a sufficient amount of additional, water is used to try and get the oocysts pass the sieve deck, the water functioning as a lubricant and to re-arrange the orientation of the (non-spherical) oocysts with regard to the deck. Any larger size of the openings would allow a more easy passage of the oocysts. Applicant found that the preferred maximum size of the openings of the first sieve deck is around Dmax. Having the openings even larger may lead to too many contaminant particles passing through the sieve deck together with the oocysts.

In another embodiment the first sieve deck has mesh openings around Dmax and the second sieve deck has mesh openings around Dmin. Applicant found that this way an adequately purified oocysts fraction can be obtained on the second sieve deck, despite the fact that any contaminant particle having a size range between Dmin and Dmax would also be likely to be captured in the residue on the second sieve deck.

In yet another embodiment the first sieve deck has mesh openings around 50 μm and the second sieve deck has mesh openings around 10 μm. Mesh openings of these sizes appear to ideally suitable to obtain a residue of highly purified oocysts of any size, even if for example the oocysts to be purified range in size between 20-35 μm in length and 20-30 μm in width. The size of the openings of the first sieve deck, 50 μm, appears to be suitable to keep out any contaminant particle on the "coarse" side, while the size of the openings of the second deck, 10 μm, appears to be suitable to keep out any contaminant particle on the "fine" side. Apparently, in the region 10 μm to 50 μm the amount of contaminant particles is so low that these particles do not lead to inadequately purified oocysts.

In an embodiment the second sieve deck is in the form of a drum, the aqueous filtrate is loaded on the inside of this drum and the drum is rotated while sieving the aqueous filtrate. In this embodiment, the residue may build up as a thin layer on the inside of this drum. This is advantageous in the further processing of the oocysts. Preferably the drum is rotated at an rpm such that the layer travels at a speed of 10 meters/minute (m/min) to 40 m/min, being the circumferential speed of the drum. Below this speed it may be that the oocysts in the layer, in particular at a low relative humidity of the gaseous environment in the drum, get too dry, while above 40 m/min the oocysts might face too much mechanical forces and get damaged.

In another embodiment the first sieve deck is in the form of a drum, the aqueous fraction is loaded on the inside of this drum and the drum is rotated while sieving the aqueous fraction. In this embodiment, the aqueous fraction may be more or less continuously added to the first sieve deck since it may have a relatively elaborate surface and is rotated continuously to allow the filtrate (containing the oocysts) to readily pas the sieve deck.

In yet another embodiment, during sieving additional aqueous medium is added to the sieve decks. This additional water may advantageously serve as a lubricant and optionally as a medium to rearrange the orientation the oocysts have with respect to the sieve deck to allow easy sieving even if the dimensions of the openings come close to Dmin. In a further embodiment the additional aqueous medium has a temperature between 19° C. and 37° C. This way, the oocysts can already start with the sporulating process while being purified from the faeces using the current sieving process. This may benefit the ultimate yield of the method. Preferably, the additional aqueous medium has a temperature around 28° C.

The system according to the invention may incorporate features to allow one or more of these embodiments of the method according to the invention to be applied. The dependent system claims recite such features.

The invention will now be explained in more detail using the following figures and examples.

EXAMPLES

FIG. 1 diagrammatically shows a system for collecting oocysts for purification.

FIG. 2 schematically shows an embodiment of a system according to the invention.

FIG. 3 schematically shows an embodiment of a sieve deck for use in a method or system according to the invention.

FIG. 4 schematically shows another embodiment of a system according to the invention.

FIG. 5 schematically shows a sieve deck for use as a support to let purified oocysts sporulate.

Example 1 describes process data regarding a method according to the invention.

FIG. 1

FIG. 1 diagrammatically shows a system for collecting animal faeces containing coccidial oocysts from host animals, and separating a coarse fraction comprising macroscopic particulate matter from the faeces and collecting a fraction containing the oocysts for further purification. In general, a number of different methods of preparing oocysts for further purification are known in the art. Any one or combination of such methods may be used prior to further purification. A preferred method is set out below.

To begin, once host animals (typically chickens) begin shedding the organism, the oocysts can be collected. Most commonly, the chickens are kept in cages (1), and are fed solid food (2) and water (3). Faeces 5 are collected from the cages, and a waste stream containing other material (feathers, straw etc) is discarded. Once collected, the faeces are brought over to a slurry tank 6 and mixed with added water (7). The resulting diluted fecal material is provided to a sieve 9 for removal of the coarse material in the faeces such as stones, remains of shavings, grid, remains of animal feed etc. For this, the sieve comprises two consecutive plate sieves, the upstream sieve having mesh openings of 2 mm, and the downstream sieve having mesh openings of 125 μm. The resulting residues (11) are discarded, and the filtrate is collected as an aqueous fraction 10 containing the oocysts.

FIG. 2

FIG. 2 schematically shows an embodiment of a system 20 according to the invention. In this embodiment the system comprises a longitudinal, tube-like housing 23 having two internal sieve decks, viz. an upstream sieve deck 21 and a downstream sieve deck 22. In this embodiment the sieve decks are made of woven stainless steel wires, according to a plain weaving pattern. The aqueous fraction 10 (see FIG. 1) is provided to the top of sieve deck 21 in order to sieve this fraction. This deck has mesh openings such that the oocysts pass to obtain an aqueous filtrate 32 comprising the oocysts, and a first residue 31 comprising particles larger than the oocysts. The aqueous filtrate 32 is provided to the top of second sieve deck 22, which sieve deck has mesh openings to obstruct passing of the oocysts through this sieve deck. This way a second residue 40 comprising the purified oocysts and a waist filtrate 42 comprising particles smaller than the oocysts is obtained.

The size of the mesh openings should be chosen to effective collect oocysts of the desired shape. For example, to collect oocysts of a size range between 15 and 25 μm, the first sieve deck may have mesh openings of 25 μm, and the second sieve deck may have mesh openings of about 14 μm. In this case, since the mesh openings correspond almost exactly with the size of oocysts, a lot of additional water may be needed (provided as a separate feed to the top of sieve deck 21) to actually have the oocysts pass the first sieve deck. In another set-up, for example to collect oocysts of a size range between 20 and 30 μm, the first sieve deck may have mesh openings of 40 μm, and the second sieve deck may have mesh openings of about 15 μm. In yet another set-up, for example to collect oocysts of a size range between 10 and 40 μm, the first sieve deck may have mesh openings of 42 μm, and the second sieve deck may have mesh openings of about 10 μm. In still another embodiment, for example to collect oocysts of a size range between 12 and 48 μm, the first sieve deck may have mesh openings of 50 μm, and the second sieve deck may have mesh openings of about 10 μm.

FIG. 3

Figure 3:
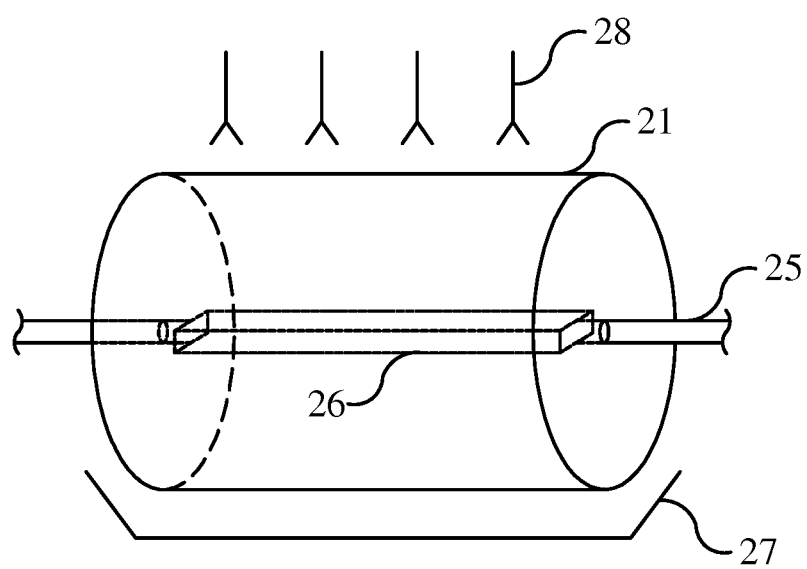

FIG. 3 schematically shows an embodiment of a sieve deck 21 (mesh openings 50 μm) for use in a method or system according to the invention. In this embodiment, the sieve deck is an endless deck in the form of a drum. The drum is rotatably supported on axis 25 and is internally provided with a stationary container 26. In use, the aqueous fraction is loaded on the inside of this drum, below the container 26, and the drum is rotated while sieving the aqueous fraction. Also, during this sieving action additional aqueous medium having a temperature of about 28° C. is added to the inside of the drum 21. The aqueous filtrate is collected in container 27. Above the drum is situated a row of spray heads 28. These heads can be used add water to the drum, either to serve as a lubricant whilst sieving, or, after the sieving has ended, to release the residue form the drum and collect it in the container 26. This container can be removed by sliding it over axis 25.

FIG. 4

Figure 4:
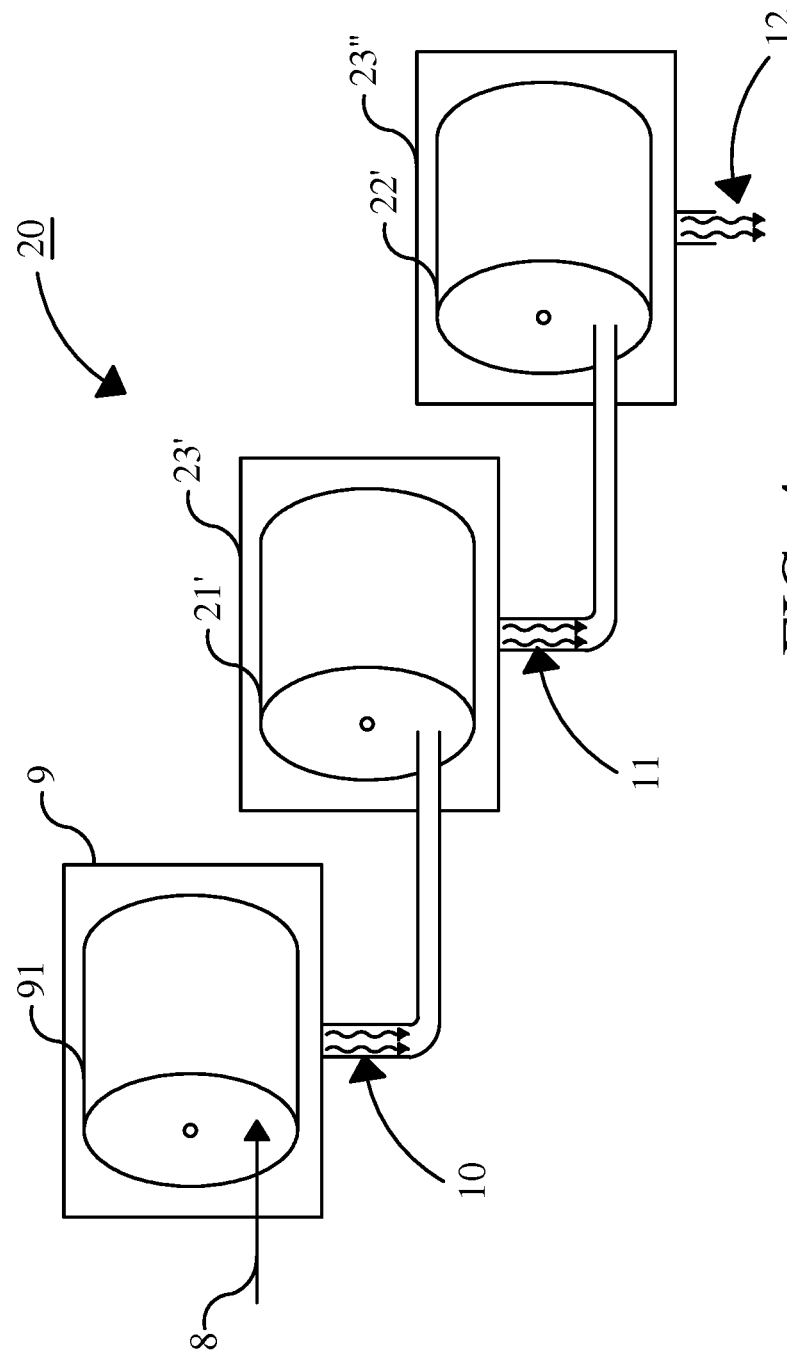

FIG. 4 schematically shows another embodiment of a system 20 according to the invention, in which embodiment a semi continuous process for applying the method according to the invention can be run. This system comprises a rotating sieve 91 (having mesh openings of 150 μm), which is surrounded by housing 9. This sieve and housing correspond to item 9 in FIG. 1. To this sieve 91 an aqueous fraction 8, comprising diluted chicken faeces (see FIG. 1, albeit that this fraction is optionally pre-sieved over a 2 mm sieve), is fed for separating the coarse fraction comprising macroscopic particulate matter from the diluted faeces. The aqueous fraction 10 containing the oocysts is collected and fed to drum-shaped rotated sieve 21' (see also FIG. 3) as present in housing 23'. As described in conjunction with FIG. 3, this sieve deck has mesh openings of 50 μm and separates the aqueous fraction in an aqueous filtrate 11 comprising the oocysts and a first residue (not shown), comprising particles larger than the oocysts. This residue can be removed as described here above. The aqueous filtrate 11 is fed to rotating sieve 22', which sieve is housed in housing 23". This sieve 22' has mesh openings of 10 μm to obstruct passing of the oocysts through this sieve deck, such that a residue comprising the purified oocysts is build up on the internal side of this drum-shaped sieve deck 22'. The waist filtrate 12 comprises particles smaller than the oocysts, such as any bacteria.

FIG. 5

Figure 5:
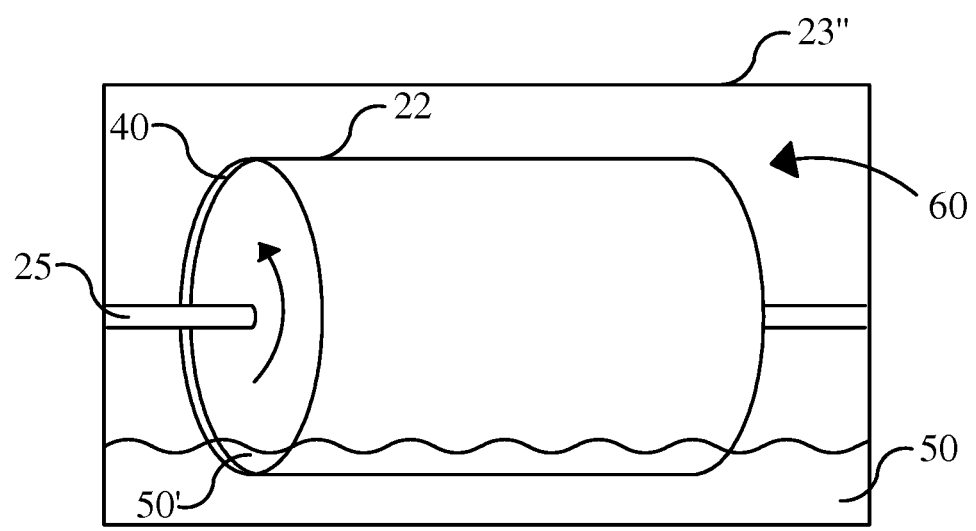

FIG. 5 schematically shows a sieve deck for use as a support to let purified oocysts sporulate. In this embodiment, the residue 40 is build up as a 2.5-3.5 mm layer on the inside of sieve deck 22 (having mesh openings of 10 μm). The drum-shaped sieve deck 22 is placed partly in a volume of water (50; kept at a temperature of 28° C.) and partly in the gaseous environment 60, such that about 20% of the total circumference of the drum is below the level of the volume of water. The drum is mounted with its longitudinal axis 25 extending in parallel with the surface of this volume of water. During sporulating the drum is rotated for maintaining the layer 40 intermittently in the oxygen containing gaseous environment 60. The drum is revolved at 10-12 rpm through the water 50'. The relative humidity of the gaseous environment in the drum is 100%. It was found that this way the oocysts can sporulate (almost all) within 48 hours.

Example 1

Example 1 describes process data regarding a method according to the invention using the system of FIG. 4. In this system small drum shaped decks are used having a length of 40 cm and a drum diameter of 80 cm (drums having a length of up to 2.80 meters and a diameter of up to 2.0 meters can be advantageously used in the set-up of FIG. 4). The decks have meshes of stainless steel wires woven according to a plain weave, with mesh openings as described in conjunction with FIG. 4. The drums rotate at 10-12 revelations per minute.

The faeces of 60 white leghorn chickens (infected with *Eimeria*) aged 26-31 days was collected (approximately 25 grams of faeces per chicken per day), mixed with 200 litres of water, and the coarse fraction was separated using a 2 mm sieve. Approximately 50 liters of this mixture (containing about 2.25 kg of faeces) was loaded into the system, wherein during sieving about 5-10 litres of water per minute was added to sieve decks 21 and 22. This resulted in about 120 grams of purified oocysts (a composition containing an estimated amount of about 85 grams of non oocysts faecal particles, typically fine sand grains, silt and clay particles, and about 35 grams of oocysts) on sieve deck 22 after 35 minutes of sieving, at a calculated yield of approximately 81% for *Eimeria acervulina* and approximately 100% for *Eimeria maxima*. Using the traditional method of flotation and centrifugation, this takes about 6 hours, with typical yields of about 50-60% for both species.

Optionally, depending on the amount of contamination still present an additional washing step may be performed by mixing the residue in a 6% hypochlorite (anti-infective) solution and load it into drum 22. Water is continuously added at about 5-10 liters per minute to remove the hypochlorite, and after 15 minutes the residue is ready for further processing.

After sporulating as described in conjunction with FIG. 5, typical sporulating rates are 85% for *Eimeria acervulina* and 90% for *Eimeria maxima* (cf typical values of 40% to a maximum of 80% for the traditional process using potassium dichromate). These sporulated oocysts can serve as antigen in a coccidiosis vaccine as known in the prior art.

The invention claimed is:

1. A method to purify coccidial oocysts having dimensions between Dmin and Dmax from faeces comprising the steps of collecting the faeces (5) containing the coccidial oocysts from host animals, diluting the faeces in an aqueous medium (7), separating a coarse fraction (11) comprising macroscopic particulate matter from the diluted faeces, and collecting an aqueous fraction (10) containing the oocysts, wherein the method further comprises sieving the aqueous fraction over a first sieve deck (21') having mesh openings to let the oocysts pass, to obtain an aqueous filtrate (11, 32) comprising the oocysts and a first residue (31) comprising particles larger than the oocysts, and automatically loading the aqueous filtrate to the inside of a second sieve deck (22'), which is rotating while sieving the aqueous filtrate, wherein the second sieve deck is drum shaped and comprises, mesh openings to obstruct passing of the oocysts through this sieve deck, to obtain a second residue (40) comprising the purified oocysts and a waste filtrate (12, 42) comprising particles smaller than the oocysts, wherein the second residue comprises the oocysts and is suitable to be used in a vaccine, and wherein the first sieve deck comprises mesh openings larger than Dmin and up to Dmax and the second sieve deck comprises mesh openings of between 0.9 to 1.1 times Dmin.

2. The method of claim 1, wherein the first sieve deck has mesh openings between 0.9 to 1.1 times 50 μm and the second sieve deck has mesh openings of between 0.9 to 1.1 times 10 μm.

3. The method of claim 1, wherein during sieving additional aqueous medium is added to the sieve decks.

4. The method of claim 3, wherein the additional aqueous medium has a temperature between 19° C. and 37° C.

5. The method of claim 4, wherein the additional aqueous medium has a temperature around 28° C.

6. The purified coccidial oocysts composition obtainable with the method of claim 1, the coccidial oocysts having dimensions between Dmin and Dmax, wherein the composition contains particles having dimensions between Dmin and Dmax and which particles a density different from the density of the oocysts.

7. The purified coccidial oocysts composition of claim 6, wherein the particles have dimensions between 10 μm and 50 μm.

8. A system (20) suitable for purifying a quantity of coccidial oocysts having dimensions between Dmin and Dmax from faeces or a fine fraction thereof, the system comprising:

a first sieve deck (21') that is drum shaped and comprises mesh openings suitable to let the oocysts pass the first sieve deck in a first filtrate (11), and obstruct particles larger than the oocysts, which particles form a first residue, a means for automatically loading the first filtrate to the inside of a second sieve deck (22'), which is rotating, wherein the second sieve deck is drum shaped, and wherein the second sieve deck comprises mesh openings to obstruct passing of the oocysts through the second sieve deck and let particles smaller than the oocysts pass to obtain a second filtrate and a second residue, wherein the second residue comprises the oocysts and is suitable to be used in a vaccine, and wherein the first sieve deck comprises mesh openings larger than Dmin and up to 1.1 times Dmax and the second sieve deck comprises mesh openings of between 0.9 to 1.1 times Dmin.

9. The system of claim 8, wherein the first sieve deck comprises mesh openings of between 0.9 to 1.1 times Dmax.

10. The system of claim 8, wherein the first sieve deck comprises mesh openings of between 0.9 to 1.1 times 50 μm and the second sieve deck comprises mesh openings of between 0.9 to 1.1 times 10 μm.

* * * * *